US006468545B1

(12) United States Patent
Doidge et al.

(10) Patent No.: US 6,468,545 B1
(45) Date of Patent: *Oct. 22, 2002

(54) TREATMENT AND PREVENTION OF HELICOBACTER INFECTION

(75) Inventors: Christopher V. Doidge, Vincent (AU); Adrian Lee, Lane Cove (AU); Fona J. Radcliff, Sydney (AU); Stuart L. Hazell, Glenfield (AU)

(73) Assignees: The University of New South Wales, Kensington (AU); CSL Limited, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/421,238

(22) Filed: Oct. 20, 1999

Related U.S. Application Data

(63) Continuation of application No. 08/695,987, filed on Aug. 15, 1996, now Pat. No. 6,005,090, which is a continuation-in-part of application No. PCT/AU95/00335, filed on Jun. 8, 1995.

(30) Foreign Application Priority Data

Jun. 8, 1994 (AU) .............................................. PM 6124

(51) Int. Cl.[7] .............................................. A61K 39/02
(52) U.S. Cl. .................. 424/234.1; 536/23.4; 536/23.5; 435/34; 435/252.1; 435/69.1
(58) Field of Search ...................... 536/23.4; 424/234.1, 424/85.8; 435/69.1, 34, 252.1

(56) References Cited

U.S. PATENT DOCUMENTS

| | | | |
|---|---|---|---|
| 5,234,910 A | | 8/1993 | Cave ............................ 514/21 |
| 5,258,178 A | * | 11/1993 | Cordle et al. ............... 424/85.8 |
| 5,260,057 A | * | 11/1993 | Cordle et al. ............... 424/85.8 |
| 5,262,156 A | | 11/1993 | Alemohammad ............ 424/92 |
| 5,420,014 A | | 5/1995 | Cripps et al. ............... 435/7.32 |
| 5,498,528 A | * | 3/1996 | King ............................ 435/34 |
| 5,538,729 A | | 7/1996 | Czinn et al. ............... 424/234.1 |
| 5,610,060 A | * | 3/1997 | Ward et al. ............... 435/252.1 |
| 5,837,240 A | * | 11/1998 | Lee et al. .................... 424/94.6 |
| 5,871,749 A | * | 2/1999 | Doidge et al. ............ 424/234.1 |
| 6,005,090 A | * | 12/1999 | Doidge et al. .............. 536/23.5 |
| 6,025,164 A | * | 2/2000 | Bolin et al. ................. 435/69.1 |

FOREIGN PATENT DOCUMENTS

| | | |
|---|---|---|
| WO | 93/16723 | 9/1993 |
| WO | 93/20843 | 10/1993 |
| WO | 94/06474 | 3/1994 |
| WO | 94/09823 | 5/1994 |
| WO | 95/27506 | 10/1995 |
| WO | 9527506 | 10/1995 |
| WO | 9533482 | 12/1995 |

OTHER PUBLICATIONS

Laszlo et al., Kazuisztika, #6 (English Translation), (1992), pp 359–361.
Monath et al., Am. J Gastroenterol, vol. 89, #393, (1994), pp 1383.
Ghiara et al., Current Opinion in Gastroenterol, vol. 11 (1), pp 52–56.
L. Kaplan, South African Medical Journal, vol. 83, (12), pp 922–923, 1993.
International Search Report for PCT/AU 95/00335.
Bazillou et al., Clin. Diagnos. lab Immun. vol. 1, #3, (1994), pp 223–226.
Newell et al., Abstract Microb Ecol.. Health Disease, vol. 4 (spec. issue), (1991), #S120 abstract.
Hawtin et al., Gen. Microbiol., vol. 136, (1990), pp 1995–2000.
Buck et al., J. Infect. Dis., vol. 153(4), (1986), pp 664–669.
Labigne et al., J. Bacteriology., vol. 173(6), (1991), pp 1920–1931.
Eaton et al., Infection & Immun., vol. 57, No. 6, (1989), pp. 110–125.
Lalor et al., Gastroenterol, vol. 196 (5 part 2), (1989), pp A283, abstract.
Westblom et al., Eur J. Clin Microbiol. Infect. Dis., vol. 11 (6), 1992), pp 522–526.
HP Worldwide Quarterly Publication, (1991), 6th Int'l Workshop on Helicobacter, p 1–8.
Stacey et al., Euro. J. Clin Microbiol. Infect. Dis., vol. 9, (1990), pp 732–737.
Czinn et al., Gastroenteral, (vol. 102) (4 pt. 2 suppl), 1992.
Bauerfeind et al., Gastroenterology (vol. 108) (4), A778, AGA abstracts.
Boslego et al., Gonorrhea vaccines, Chapter 17, Vaccines and immunotherapy, (1991), pp 211–223.
Mai et al., J. Clin Invest., vol. 87, (1991), pp 894–900.
Marshall et al., J. of Gastroenterol and Hepatology, vol. 6, (1991), pp 121–124.
Doig et al., Infect. and Immun., vol. 62(10), (1994), pp 4526–4533.
Czinn et al., Infect. and Immunity, (1991), pp 2359–2363.
Newell et al, Basic and Clinical Aspects of H.pylori infection, pp. 223–226, Springer Verlag Berlin Heidelberg, 1994.*
Sugiyama, T et al, Gastroenterology, vol. 110(4 suppl), p. A266, col. 2, top of page, May 19–22, 1996.*

(List continued on next page.)

Primary Examiner—Lynette R. F. Smith
Assistant Examiner—Ginny Allen Portner
(74) Attorney, Agent, or Firm—Foley & Lardner

(57) ABSTRACT

An antigenic preparation for use in the treatment of prevention of Helicobacter infection in a mammalian host, comprises the catalase enzyme of Helicobacter bacterial, particularly the catalase enzyme of H. pylori or H. felis, or an immunogenic fragment thereof.

20 Claims, No Drawings

OTHER PUBLICATIONS

Jiang, Q. et al, May, Molecular Microbiology, vol. 20(4), pp. 833–842, 1996.*

Heap, K et al., Micro. Health Dis, vol. 4, p. S119, Vth International Workshop on Campylobacter, Helicobacter and related organisms, Oct. 7–10, 1991.*

Rappuoli, R et al, European J. Gastroenterol. Hepatology, vol. 5 (suppl 2), pp. S76–S78, 1993.*

Dunkley, M.L et al, Microb. Ecol. Health Dis. vol. 4, (spec issue), p. S148, 1991.*

Odenbreit, S et al, Dec. 1996, vol. 178(23), pp. 6960–6967, Journal of Bacteriology, Dec. 1996.*

Hazell, SL et al, J. Clinical Microbiology vol. 28(5), May 1990, pp. 1060–1061, May 1990.*

* cited by examiner

TREATMENT AND PREVENTION OF HELICOBACTER INFECTION

CROSS-REFERENCE TO RELATED APPLICATIONS

This application is a continuation of application Ser. No. 08/695,987, filed Aug. 15, 1996 now U.S. Pat. No. 6,005,090, which is a Continuation-In-Part of PCT/AU95/00335, filed Jun. 8, 1995.

FIELD OF THE INVENTION

This invention relates to protective Helicobacter antigens, especially *H. pylori* antigens, and to the use of these antigens for the treatment and prevention of gastroduodenal disease associated with *H. pylori* infection in humans.

BACKGROUND OF THE INVENTION

*Helicobacter pylori* is a bacterium that infects the stomach lining (or gastric mucosa) of perhaps half the world's population. Spiral organisms were first microscopically observed in human gastric mucosa in 1906. However, *H. pylori* was not successfully cultured until 1982. Infection with the organism is usually chronic, and results in continuing inflammation of the gastric mucosa. The infection is often asymptomatic. However, in association with other cofactors, a proportion of infected people go on to develop sequelae including peptic ulceration of the stomach or duodenum, gastric adenocarcinomas and gastric lymphomas. Peptic ulcer treatment studies have shown that cure of *H. pylori* infection is associated with a dramatic reduction in the relapse rate of this usually chronic disease. Long term infection with *H. pylori* leads to the development of chronic atrophic gastritis, which has long been recognised as a precursor lesion in the development of gastric cancer. Thus a number of studies have now linked preceding *H. pylori* infection with an increased risk of developing gastric cancer. Therefore eradication of current infection and prevention of new infection with this organism has the potential to significantly reduce the incidence of diseases that result in considerable morbidity and mortality[1,2].

Infection with *H. pylori* is difficult to treat. Current experimental therapies for treating the infection have problems with efficacy and significant levels of adverse effects. There are no prophylactic measures available. A solution to both the prevention and treatment of *H. pylori* infection would be the development of an immunogenic preparation that, as an immunotherapeutic, treated established infections, and as a vaccine, prevented the establishment of new or recurrent infections. Such a preparation would need to induce effective immune responses to protective antigens, while avoiding inducing responses to self antigens or other potentially harmful immune responses. This may be achieved by identifying the specific protective component or components and formulating immunotherapeutic or vaccine preparations including these component(s).

The identification of such protective components of an organism, is often accomplished through the use of an animal model of the infection. Initially, *H. pylori* did not naturally infect laboratory animals. However, an animal model of human *H. pylori* infection has been developed using a closely related organism, *H. felis*, and specific pathogen free (SPF) mice[3]. These organisms are able to colonise the gastric mucosa of SPF mice, where they establish a chronic infection with many of the features of *H. pylori* infection in humans. *H. felis* infection in the mice induces a chronic gastritis and a raised immune response. As in the human case, this response is not effective in curing the infection.

This model has been used to demonstrate that oral treatment of *H. felis* infected mice with a preparation containing disrupted *H. pylori* cells and cholera toxin as a mucosal adjuvant, can cure a significant portion of infected mice[4]. This effect is likely to be mediated through an immune response to a cross-reactive antigen possessed by each of the closely related species.

In working by the inventors leading to the present invention, these cross-reactive antigens were recognised by performing a Western blot using *H. pylori* disrupted cells as the antigen, and probing the blot with serum from ice immunised with *H. felis* and cholera toxin adjuvant. Sections of membrane containing proteins recognised as cross-reactive were removed from the membrane, the proteins bound to them were eluted, and their N-terminal amino acid sequence determined by microsequencing.

The N-terminal amino acid sequence of one of the two proteins that successfully yielded sequence data closely matched the previously published sequence of the microbial enzyme, urease[5]. This enzyme has already been shown to be a protective antigen when used in a vaccine to prevent infection.

The N-terminal amino acid sequence of the other protein closely matched the previously published N-terminal sequence of the microbial enzyme, catalase[6]. This enzyme has not previously been shown to be a protective antigen of *H. pylori*.

International Patent Application No. PCT/FR95/00383 (Publication No. WO 95/27506) in the name Pasteur Merieux Serums et Vaccins, published Oct. 19, 1995, discloses an *H. pylori* immunising composition, based on proposed use of *H. pylori* catalase in substantially purified form as an immunising substance useful for prophylactic or therapeutic purposes. It is suggested that the catalase could be obtained either by extraction from *H. pylori* (using the purification method of Hazell et al.[10]) or by recombinant means. The disclosure contains no supporting data showing efficacy of *H. pylori* catalase in use as an immunising substance, nor is there any supporting disclosure or teaching of the preparation of *H. pylori* catalase by recombinant means or of the efficacy of recombinant catalase in use as an immunising substance.

Recently, an *H. pylori* (Sydney strain)/mouse model of human *H. pylori* infection has been developed and used by the present inventors to confirm that catalase, in particular recombinant catalase, has utility as a protective antigen.

SUMMARY OF THE INVENTION

In one aspect, the present invention provides an antigenic preparation for use in the treatment or prevention of Helicobacter inflection, which comprises an at least partially purified preparation of the catalase of Helicobacter bacteria.

The term "at least partially purified" as used herein denotes a preparation in which the catalase content is greater, preferably at least 30% and more preferably at least 50% greater, than the catalase content of a whole cell sonicate of Helicobacter bacteria. Preferably, the preparation is one in which the catalase is "substantially pure", that is one in which the catalase content is at least 80%, more preferably at least 90%, of the total Helicobacter antigens in the preparation.

Accordingly, in a particularly preferred embodiment, the present invention provides an antigenic preparation for use in treatment or prevention of Helicobacter infection, which comprises substantially pure catalase of Helicobacter bacteria. Such a preparation may be prepared as a recombinant catalase by techniques described hereinafter.

In another aspect, the present invention provides an isolated Helicobacter antigen for use in the treatment or prevention of Helicobacter infection in a mammalian host, which comprises the catalase of Helicobacter bacteria, or an immunogenic fragment thereof.

The term "isolated" as used herein denotes that the antigen has undergone at least one purification or isolation step, and preferably is in a form suitable for use in a vaccine composition.

It is to be understood that the present invention extends not only to an antigenic preparation or isolated antigen comprising the catalase of Helicobacter bacteria, but also to antigenic preparations comprising immunogenic fragments of this catalase, that is catalase fragments which are capable of eliciting a specific protective immune response in a mammalian host. Such immunogenic fragments may also be recognised by Helicobacter-specific antibodies, particularly monoclonal antibodies which have a protective or therapeutic effect in relation to Helicobacter infection or polyclonal antibodies contained in immune sera from mammalian hosts which have been vaccinated against Helicobacter infection.

In another aspect, the present invention provides a vaccine composition for use in the treatment or prevention of Helicobacter infection in a mammalian host, which comprises an immunologically effective amount of an antigenic preparation or isolated antigen as broadly described above, optionally in association with an adjuvant, together with one or more pharmaceutically acceptable carriers and/or diluents.

In yet another aspect, the present invention provides a method for the treatment or prevention of Helicobacter infection in a mammalian host, which comprises administration to said host of an immunologically effective amount of an antigenic preparation or isolated antigen as broadly described above, optionally in association with an adjuvant.

In a related aspect, this invention provides the use of a vaccine composition comprising an immunologically effective amount of an antigenic preparation or isolated antigen as broadly described above, optionally in association with an adjuvant, for the treatment or prevention of Helicobacter infection in a mammalian host.

In yet another aspect, the invention provides the use of an antigenic preparation or isolated antigen as broadly described above, optionally in association with an adjuvant, in the manufacture of a vaccine composition for the treatment or prevention of Helicobacter infection in a mammalian host.

Preferably, but not essentially, the antigenic preparation or isolated antigen of this invention is orally administered to the host, an is administered in association with a mucosal adjuvant. However, the invention also extends to parenteral administration of this antigenic preparation or isolated antigen.

By use of the term "immunologically effective amount" herein in the context of treatment of Helicobacter infection, it is meant that the administration of that amount to an individual infected host, either in a single dose or as part of a series, that is effective for treatment of Helicobacter infection. By the use of the term "immunologically effective amount" herein in the context of prevention of Helicobacter infection, it is meant that the administration of that amount to an individual host, either in a single dose or as part of a series, that is effective to delay, inhibit or prevent Helicobacter infection. The effective amount varies depending upon the health and physical condition of the individual to be treated, the taxonomic group of individual to be treated, the capacity of the individual's immune system to synthesise antibodies, the degree of protection desired, the formulation of the vaccine, the assessment of the medical situation, and other relevant factors. It is expected that the amount will fall in a relatively broad range that can be determined through routine trials.

Preferably, the catalase antigen above comprises an amino acid sequence substantially corresponding to the deduced sequence of the catalase gene from isolate RU1 or isolate 921023 hereinafter (SEQ ID NO.2 or 4), or allelic or other variants thereof. Suitable variants may have at least 50–60%, more preferably at least 70–80%, and most preferably at least 90%, similarity to one of the amino acid sequences referred to above, or to a region or part thereof, provided the variant is capable of eliciting a specific protective immune response in a mammalian host.

As described above, the present invention extends not only to the particular catalase antigen of Helicobacter bacteria as described above, but also to immunogenic fragments of the particular antigen, that is fragments of the antigen which are capable of eliciting a specific protective immune response in a mammalian host. Suitably, the immunogenic fragment will comprise at least five, and more preferably at least ten, contiguous amino acid residues of the particular antigen. Such immunogenic fragments may also be recognised by Helicobacter-specific antibodies, particularly antibodies which have a protective or therapeutic effect in relation to Helicobacter infection.

The present invention also extends to an antibody, which may be either a monoclonal or polyclonal antibody, specific for an antigenic preparation or an isolated Helicobacter antigen as broadly described above. Such antibodies may be produced by methods which are well known to persons skilled in this field.

In this aspect, the invention further provides a method for the treatment or prevention of Helicobacter infection in a mammalian host, which comprises passive immunisation of said host by administration of an effective amount of an antibody, particularly a monoclonal antibody, specific for an antigenic preparation or an isolated Helicobacter antigen as broadly described above.

The Helicobacter antigenic preparation or isolated antigen of this invention may be prepared by purification or isolation from natural sources, such as a whole cell sonicate of Helicobacter bacteria. Alternatively, however the antigenic preparation or isolated antigen may be prepared by synthetic, preferably recombinant, techniques. When prepared by recombinant techniques, the antigen may have an amino acid sequence substantially identical to the naturally occurring sequence or may contain one or more amino acid substitutions, deletions and/or additions thereto provided that following such alterations to the sequence, the molecule is still capable of eliciting a specific protective immune response against the naturally occurring Helicobacter antigen. A similar immunogenic requirement is necessary for any fragments or derivatives of the antigen whether made from the recombinant molecule or the naturally occurring molecule. Accordingly, reference herein to a Helicobacter antigen is considered reference to the naturally occurring molecule, its recombinant form and any mutants, derivatives, fragments, homologues or analogues thereof provided that such molecules elicit a specific protective immune response against the naturally occurring Helicobacter antigen. Also included are fusion molecules between two or more Helicobacter antigens or with other molecules including fusion molecule with other molecules such as glutahione-S-transferase (GST) or β-galactosidase.

The present invention also extends to an isolated nucleic acid molecule encoding a helicobacter catalase antigen and preferably having a nucleotide sequence as set forth in SEQ ID NO. 1 or 3, or being substantially similar to all or a part thereof. The term "substantially similar" means having at least 40–50%, more preferably at least 60–70%, and most preferably at least 80% identity. A "part" in this context means a contiguous series of at least 15 nucleotides, and more preferably at least 25 nucleotides.

According to this embodiment, there is provided a nucleic acid molecule comprising a sequence of nucleotides which encodes a Helicobacter catalase antigen and hybridises under low stringency conditions to all or part of a nucleic acid sequence set forth in SEQ ID NO. 1 or 3, or to a complementary form thereof.

In another aspect, this invention provides a nucleic acid molecule comprising a sequence of nucleotides substantially as set forth in SEQ ID NO. 1 or 3, or a part thereof.

The nucleic acid molecule may be RNA or DNA, single stranded or double stranded, in linear or covalently closed circular form. For the purposes of defining the level of stringency, reference can conveniently be made to Sambrook et al. (1989) at pp 387–389 which is herein incorporated by reference where the washing step at paragraph 11 is considered high stringency. A low stringency is defined herein as being in 0.1–0.5 w/v SDS at 37–45° C. for 2–3 hours. Depending on the source and concentration of nucleic acid involved in the hybridisation, alternative conditions of stringency may be employed such as medium stringent conditions which are considered herein to be 0.25–0.5% w/v SDS at ≧45° C. for 2–3 hours or high stringent conditions as disclosed by Sambrook et al. (1989).

It will be appreciated that the sequence of nucleotides of this aspect of the invention may be obtained from natural, synthetic or semi-synthetic sources; furthermore, this nucleotide sequence may be a naturally-occurring sequence, or it may be related by mutation, including single or multiple base substitutions, deletions, insertions and inversions, to such a naturally-occurring sequence, provided always that the nucleic acid molecule comprising such a sequence is capable of being expressed as a Helicobacter antigen as broadly described above.

The nucleotide sequence may have expression control sequences positioned adjacent to it, such control sequences usually being derived from a heterologous source.

This invention also provides a recombinant DNA molecule comprising an expression control sequence having promoter sequences and initiator sequences and a nucleotide sequence which codes for a Helicobacter catalase antigen, the nucleotide sequence being located 3' to the promoter and initiator sequences. In yet another aspect, the invention provides a recombinant DNA cloning vehicle capable of expressing a Helicobacter catalase antigen comprising an expression control sequence having promoter sequences and initiator sequences, and a nucleotide sequence which codes for a Helicobacter catalase antigen, the nucleotide sequence being located 3' to the promoter and initiator sequences. In a further aspect, there is provided a host cell containing a recombinant DNA cloning vehicle and/or a recombinant DNA molecule as described above.

Suitable expression control sequences and host cell/ cloning vehicle combinations are well known in the art, and are described by way of example, in Sambrook et al. (1989).

In yet further aspects, there is provided fused polypeptides comprising a Helicobacter catalase antigen of this invention and an additional polypeptide, for example a polypeptide coded for by the DNA of a cloning vehicle, fused thereto. Such a fused polypeptide can be produced by a host cell transformed or infected with a recombinant DNA cloning vehicle as described above, and it can be subsequently isolated from the host cell to provide the fused polypeptide substantially free of other host cell proteins.

The present invention also extends to synthetic polypeptides displaying the antigenicity of a Helicobacter catalase antigen of this invention. As used herein, the term "synthetic" means that the polypeptides have been produced by chemical or biological means, such as by means of chemical synthesis or by recombinant DNA techniques leading to biological synthesis. Such polypeptides can, of course, be obtained by cleavage of a fused polypeptide as described above and separation of the desired polypeptide from the additional polypeptide coded for by the DNA of the cloning vehicle by methods well known in the art. Alternatively, once the amino acid sequence of the desired polypeptide has been established, for example, by determination of the nucleotide sequence coding for the desired polypeptide, the polypeptide may be produced synthetically, for example by the well-known Merrifield solid-phase synthesis procedure.

Once recombinant DNA cloning vehicles and/or host cells expressing a Helicobacter catalase antigen of this invention has been identified, the expressed polypeptides synthesised by the host cells, for example, as a fusion protein, can be isolated substantially free of contaminating host cell components by techniques well known to those skilled in the art.

Isolated polypeptides comprising, or containing in part, amino acid sequences corresponding to a Helicobacter catalase antigen may be used to raise polyclonal antisera by immunising rabbits, mice or other animals using well established procedures. Alternatively, such polypeptides may be used in the preparation of monoclonal antibodies by techniques well known in the art.

In addition, the polypeptides in accordance with this invention including fused polypeptides may be used as an active immunogen in the preparation of single or multivalent vaccines by methods well known in the art of vaccine manufacture for use in the treatment or prevention of Helicobacter infection in a mammalian host.

Alternatively, the polypeptides in accordance with the present invention including fused polypeptides may be used as antigen in a diagnostic immunoassay for detection of antibodies to Helicobacter in a sample, for example, a serum sample from a human or other mammalian patient. Such immunoassays are well known in the art, and include assays such as radioimmunoassays (RIA) and enzyme-linked immunosorbent assays (ELISA).

The present invention also extends to delivery to the host using a vector expressing the catalase of Helicobacter bacteria, or an immunogenic fragment thereof. Accordingly, in a further aspect this invention provides a preparation or use in the treatment ore prevention of Helicobacter infection in a mammalian host, which comprises a vector expressing the catalase of Helicobacter bacteria or an immunogenic fragment thereof.

In this aspect, the invention extends to a method for the treatment or prevention of Helicobacter infection in a mammalian host, which comprises administration to said host of a vector expressing the catalase of Helicobacter bacteria or an immunogenic fragment thereof.

Further, the invention extends to the use of a vector expressing the catalase of Helicobacter bacteria or an immunogenic fragment thereof, for the treatment or prevention of Helicobacter infection in a mammalian host.

Throughout this specification, unless the context requires otherwise, the word "comprise", or variations such as "comprises" or "comprising", is to be understood to imply the inclusion of a stated integer or group of integers but not the exclusion of any other integer or group of integers.

DETAILED DESCRIPTION OF THE INVENTION

Preferably, the antigen preparation or isolated antigen of this invention comprises the catalase of *H. pylori* or *H. felis*, most preferably *H. pylori* catalase. Preferably also, this antigenic preparation or isolated antigen is used in a vaccine composition for oral administration which includes a mucosal adjuvant.

In a particularly preferred aspect of this invention, an oral vaccine composition comprising substantially pure *H. pylori* catalase, more preferably recombinant *H. pylori* catalase, in association with a mucosal adjuvant is used for the treatment or prevention of *H. pylori* infection in a human host.

The mucosal adjuvant which is optionally, and preferably, administered with the Helicobacter catalase preparation or antigen to the infected host is preferably cholera toxin. Mucosal adjuvants other than cholera toxin which may be used in accordance with the present invention include non-toxic derivates of cholera toxin, such as the B sub-unit (CTB), chemically modified cholera toxin, or related proteins produced by modification of the cholera toxin amino acid sequence. These may be added to, or conjugated with, the Helicobater catalase preparation or antigen. The same techniques can be applied to other molecules with mucosal adjuvant or delivery properties such as *Escherichia coli* heat labile toxin. Other compounds with mucosal adjuvant or delivery activity may be used such as bile; polycations such as DEAE-dextran dextran and polyomithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine.

The Helicobacter catalase preparation or antigen may be delivered in accordance with this invention in ISCOMS (immune stimulating complexes), ISCOMS containing CTB, liposomes or encapsulated in compounds such as acrylates or poly(DL-lactide-co-glycoside) to form microspheres of a size suited to adsorption by M cells. Alternatively, micro or nanoparticles may be covalently attached to molecules such as vitamin B12 which have specific gut receptors. The Helicobacter catalase preparation or antigen may also be incorporated into oily emulsions and delivered orally. An extensive though not exhaustive list of adjuvants can be found in Cox and Coulter[7].

Other adjuvants, as well as conventional pharmaceutically acceptable carriers, excipients, buffers or diluents, may also be included in the prophylactic or therapeutic vaccine composition of this invention. The vaccine composition may, for example, be formulated in enteric coated gelatine capsules including sodium bicarbonate buffers together with the Helicobacter catalase preparation or antigen and cholera toxin mucosal adjuvant.

The formulation of such therapeutic compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

As an alternative to the delivery of the Helicobacter catalase preparation or antigen in the form of a therapeutic or prophylactic oral vaccine composition, the catalase or an immunogenic fragment thereof may be delivered to the host using a live vaccine vector, in particular using live recombinant bacteria, viruses or other live agents, containing the genetic material necessary for the expression of the catalase or immunogenic fragment as a foreign antigen. Particularly, bacteria that colonise the gastrointestinal tract, such as Salmonella, Yersinia, Vibrio, Escherichia and GCG have been developed as vaccine vectors, and these and other examples are discussed by Holmgren et al.[8] and McGhee et al.[9].

The Helicobacter catalase preparation or antigen of the present invention may be administered as the sole active immunogen in a vaccine composition or expressed by a live vector. Alternatively, however, the vaccine composition may include or the live vector may express other active immunogens, including other Helicobacter antigens such as urease or the lipopolysaccharide (LPS) of Helicobacter bacteria (see International Patent Application No. PCT/AU95/00077), as well as immunologically active antigens against other pathogenic species.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

Data obtained from Western blots mentioned above, show that *H. pylori* catalase is recognised by the serum of mice vaccinated with an *H. felis* antigen preparation (pulse cholera toxin adjuvant). These mice can be shown to be protected against *H. felis* infection. This data indicates the use of *H. pylori* catalase as a protective antigen in human *H. pylori* infection, and purified or recombinant catalase may be used as an antigenic component of a therapeutic or prophylactic vaccine, either on its own, or in combination with other antigens, carriers, adjuvants, delivery vehicles or excipients.

Further details of the present invention are set out, by way of illustration only, in the following Examples. It is to be understood, however, that this detailed description is included solely for the purposes of exemplifying the present invention, and should not be understood in any way as a restriction on the broad description of the invention as set out above.

EXAMPLE 1

A. Methods

Sonicated *H. pylori* cells (strain HP 921023) were separated in a 12% discontinuous (i.e. homogeneous) SDS-PAGE gel under denaturing conditions using a Mini-Protean II apparatus (Bio-Rad). Proteins were transferred from the gel to ProBlott (Applied Biosciences PVDF-polyvinylidene difluoride) membrane using CAPS buffer (3-(cyclohexylamino)-1-proanesulphonic acid buffer) in a Mini transblot system (Bio-Rad).

Strips were removed from the ends of the PVDF and reacted with immune sera from mice vaccinated with *H. felis* plus cholera toxin and traced with an HRP labelled anti-mouse sera and developed using 4-chloro-1-naphthol as per standard Western blot methods. The remainder of the PVDF was stained with Coomassie blue (Bio-Rad) to visualise the protein bands. Six proteins recognised by the immune sera were selected and the corresponding Coomassie stained bands on the PVDF were carefully excised for sequencing.

The six excised bands of PVDF were cut into small pieces (approx. 0.5 cm long) and placed into the reaction cartridge of an Applied Biosystems Model 476A Protein Sequencer System. All chemistry, HPLC separations, data quantitation and protein sequencing reporting is automatically carried out in this system.

B. Results

Four samples gave no signal in the Protein Sequencer System. Two samples gave clear amino acid sequence data: sample 5, an approximately 53 kD protein (±10%), and sample 3, an approximately 66 kD protein (±10%). This data is shown below.

(i) Sample 3:

DDN

MKKIVFKEYV (SEQ ID No. 5)

AP

Note: the first three cycles gave equivocal results.

The sequence data of sample 3 corresponds closely, but not exactly, with the previously published N-terminal sequence for the enzyme urease[5]. This enzyme has been shown to be a protective antigen in studies using the *H. felis*/mouse model.

(ii) Sample 5:

MVNKDVKQTTAFGTP (SEQ ID No. 6)

The sequence data of sample 5 corresponds closely, with one difference, to the previously published N-terminal sequence of the enzyme catalase[6]. This enzyme has not previously been shown to be a protective antigen however the fact that the enzyme is recognised by the immune serum of mice vaccinated with an *H. felis* antigen preparation to protect against *H. felis* infection, combined with the fact that mice vaccinated with an *H. pylori* antigen preparation are protected against *H. felis* infection, indicates the *H. pylori* catalase as a protective antigen in *H. pylori* infection in humans.

EXAMPLE 2

1. Purification of *H. Pylori* Catalase[10]

Approximately 60 plates (CSA) of *H. pylori* (clinical strain 921023) were grown in 10% $CO_2$ at 37° C. for 48 hours. All following steps until loading on the column were undertaken on ice. The *H. pylori* cells were harvested in 0.1 M sodium phosphate buffer pH 7.2 and the suspension spun down gently and resuspended in no more than 5 mL of 0.1 M sodium phosphate buffer. The suspension was then sonicated at 6 kHz 40% duty cycle for 5 minutes. Following this, the sonicate was spun for 5 minutes at 10,000 g, the supernatant collected and passed through a 0.22 μm filter into a sterile container.

The filtrate was loaded onto a K26/100 gel filtration column of Sephacryl S-300 HR and eluted using sodium phosphate buffer at a flow rate of 1.0 mL min$^{-1}$. The eluate was collected into fractions (100 drops/fraction) and those containing catalase identified by testing for catalase activity (1 drop of the fraction placed in $H_2O_2$ diluted 1:10 in distilled water and examined for bubbling). Fractions containing the strongest catalase activity were pooled then diluted 1:10 in 0.01M sodium phosphate (filtered). The fractions were then run through a MEMSEP 1000 cm ion exchange capsule. 100 mL of the 0.01 M sodium phosphate buffer was then run through the ion exchange capsule to remove any excess proteins. 1 M NaCl in 0.1 M sodium phosphate buffer was run through the ion exchange capsule to elute out the catalase. Catalase positive fractions were identified by their strong yellow colour and confirmed by testing for a bubbling reaction in $H_2O_2$.

The catalase positive fractions were stored at 4° C. and protected from light. Each fraction was tested for protein concentration using the Bio-Rad DC protein assay, and selected for immunising mice if it contained over 1.5 mg/mL of protein. Prior to immunising mice the purified catalase was checked for contaminants using 12% SDS-PAGE. Proteins were visualised by staining with Coomassie Blue, which indicated that the catalase preparation was at least 95% pure. Image analysis indicated that the catalase's molecular weight was 52–53 kDa. The purified catalase was also strongly recognised by a catalase monoclonal antibody.

2. Immunisation with *H. Pylori* Catalase

Sufficient purified catalase for Immunising 10 mice was obtained and pooled. Mice were given 0.2 mg purified catalase+10 μg cholera toxin (CT) 4 times on days 0, 7, 14 and 21. Control groups were given cholera toxin alone or PBS buffer alone. The dose size was 150 μl for all groups. On the day of each immunising dose, the catalase was checked for activity using$_2$ and for any signs of degradation using SDS-PAGE and Coomassie Blue staining. No signs of declining activity or any degradation was observed throughout the immunisation course. Three weeks after the last immunising dose all groups were challenged twice with ~10$^H$ H. felis. Three weeks later mice were euthanased and samples (sera, saliva, bile and the stomach—half for histology and half the antrum for the direct urease test) were collected Experiment Outline

| TIME (days) | CATALASE CT (10 Mice) | CT ALONE (10 mice) | PBS ALONE (10 mice) |
| --- | --- | --- | --- |
| 0 | Cat + CT | CT alone | PBS alone |
| 7 | Cat + CT | CT alone | PBS alone |
| 14 | CAT + CT | CT alone | PBS alone |
| 21 | Cat + CT | CT alone | PBS alone |
| 42 | H. felis Challenge | H. felis Challenge | H. felis Challenge |
| 44 | H. felis Challenge | H. felis challenge | H. felis Challenge |
| 65 | Collect 10 | Collect 10 | Collect 10 |

3. Results
Urease

| POSITIVE UREASE RESULT (%) | | |
|---|---|---|
| Catalase + CT (10) | CT alone (10) | PBS alone (10) |
| 0/10 (0) | 7/10 (70) | 10/10 (100) |

Western Blotting

Western blots of sera from mice showed strong recognition of *H. pylori* catalase by the immunised mice, whereas mice from the other groups showed weak or absent recognition.

Persons skilled in this art will appreciate that variations and modifications may be made to the invention as broadly described herein, other than those specifically described without departing from the spirit and scope of the invention. It is to be understood that this invention extends to include all such variations and modifications

EXAMPLE 3

Cloning, Purification and Testing in an *H. pylori* Animal Model of Recombinant *H. pylori* Catalase as a Protective Antigen The catalase gene has been cloned from each of two different isolates of *H. pylori*, isolate RU1 and isolate 921023.

1. Identification of E. coli Clones Expressing Catalase From H. pylori Isolate 921023.

1.1 Materials and Methods 1.1.1 Bacterial Strains

Helicobacter pylori strain HP921023 was used as the DNA donor for preparing the gene library. *Escherichia coli* strain ER1793 (New England Biolabs) was the host used for phage infection and planting of Lambda ZAP Express. *E. coli* strains XL 1-Blue MRF' and XLOLR (Stratagene) were used for excision of phagemid pBK-CMV and protein expression of the cloned gene.

1.1.2 Isolation of *H. pylori* chromosomal DNA

Whole cell DNA from *H. pylori* was prepared essentially as reported by Majewski and Goodwin".

1.1.3 Antisera Preparation

Mouse antisera was raised against *Helicobacter pylori* by four oragastric immunisations at weekly intervals. Each vaccine dose consisted of 1 mg (protein of sonicated *H. pylori* and 10 μg of cholera toxin. Blood was collected and serum pooled. This serum was absorbed with 50% v/v *E. coli* extract (Promega) containing 5% w/v skim milk and 0.05% v/v Tween 20 in TBS at a final dilution of 1:100. The preparation was incubated at room temperature for 4 hours prior to immunoscreening to eliminate non-specific reactivity of antisera with host proteins. The specificity of the sera was confirmed by dot blot and Western blotting using dilutions of whole cells of *H. pylori* for positive control and *E. coli* XLOLR as the negative control.

1.1.4 Bacterial Growth Conditions

For infection with Lambda ZAP Express, strain ER1793 cells were initially grown in Luria-Bertanl (LB) broth supplemented with 0.2% w/v maltose and 10 mM $MgSO_4$ at 20° C. Following infection, cells were maintained in LB broth at 37° C. for 15 minutes and then plated on NZY agar medium and incubated at 42° C. for 4 hours then at 37° C. overnight. For phagemid excision and plasmid isolation *E. coli* strains XL1-Blue and XLOLR were grown in LB broth at 37° C., and transformed XLOLR cells selected on LB/Kanarnycin plates (50 μg/mL) at 37° C.

1.1.5 Construction of *H. pylori* Gene Library

An *H. pylori* expression library was constructed using standard procedures [12], in the Lambda ZAP express vector (Stratagene) which had been predisgested with BamHI and the terminal 5' phosphates removed with calf intestinal phosphatase. Genomic DNA partially digested with Sau3AI, was fractionated by gel electrophoresis and DNA fragments between 6 to 12 kb were isolated. This DNA was ligated with 1.0 μg of BamHI-digested lambda arms. Recombinant phage DNA was packaged in vitro using Gigapack II extracts (Stratagene). The library was titred by infecting *E. coli* strain ER1793 or XL1-Blue MRF' cells with aliquots of packaged phage and plated onto indicator plates containing IPTG and X-gal. The ratio of non-recombinant phage to recombinant phage was 1:5. The titre of the recombinant library was calculated to be $1 \times 10^6$ pfu per μg of lambda DNA.

1.1.6 Screening of *H. pylori* Library for the Gene Coding for Catalase

A portion of the *H. pylori* gene library was screened by DNA hydridization techniques using a cloned probe comprising approximately 200 bp from the *H. pylori* catalase coding sequence beginning at nucleotide 410. A total of 8000 plaques were plated (4000 bacteriophage plaques per plate) and lifted onto nitrocellulose filters for DNA hybridization analysis with a P-labelled probe. When a positive phage clone was identified, an agar plug containing the plaque was picked and phage eluted into SM buffer. To obtain plaque purity the processes of infecting bacteria, replating and hybridization were repeated.

1.1.7 In vivo Excision of Plasmid pBK-CMV Lambda ZAP Express Vector

In vivo excision of pBK-CMV containing *H. pylori* DNA from lambda ZAP Express was achieved by infecting *E. coli* strain XL1-Blue MRF' simultaneously with Lambda ZAP Express containing insert DNA and ExAssist helper phage M13. Excised phagemids were packaged as filamentous phage particles and secreted from host cells, which were subsequently heat killed. The phagemids were rescued by infecting XLOLR cells and plating onto LB/Kanamycin (50 μg/mL) plates. Bacterial colonies appearing on plates contained pBK-CMV double-stranded phagemid with the cloned DNA insert from *H. pylori*. These colonies were then analysed for catalase expression.

1.1.8 SDS-PAGE and Western Blot Analysis

The proteins produced by these potentially *H. pylori* catalase clones in *E. coli* XLOLR were analysed by standard SDS-PAGE and Western Blot techniques [12, 13]. 10 mL cultures of XLOLR containing expression plasmid were grown in supermedium at 37° C. overnight. Cultures were induced with IPTG to a final concentration of imM, with continued incubation for 2–4 h. Aliquots of 1 mL were collected, cells pelleted by centrifugation and resuspended in 10 mM Tris-HCl (pH 8). Cells were mixed with equal valume of SDS sample reducing buffer and boiled for 10 minutes. Proteins were resolved by electrophoresis on 4–20% gradient Tris-glycine gels (Novex) and electrotransferred onto nitrocellulose membrane (BioRad) for detection of immunoreactive proteins of *H. pylori* using anti-*H. pylori* mouse sera as described above.

1.1.9 Catalase Activity Assay

Colonies of candidate clones were grown on LB/Kanamycin (50 µg/mL) plates following which 100 µl of hydrogen peroxide was applied to each colony. A positive result was indicated by a characteristic bubbling of the cells due to the degradation of substrate and the release of oxygen.

1.1.10 DNA Sequencing

DNA sequence analysis was performed by manual sequencing on both strands of plasmid DNA by primer walk using the dideoxynecleotide chain termination method[14].

1.1.11 Plasmid DNA Preparation

Plasmid DNA was isolated by the alkaline lysis method[12] from cultures of *E. coli* XLOLR clones. Restriction enzyme digestion were performed as recommended by the enzyme manufacturer (Promega Inc.).

1.2 Results and Discussion

To enable isolation of lcones bearing the complete *Helicobacter pylori* catalase gene, a genomic library of strain HP921023 was constructed in the lambda expression vector lambda ZAP Express. This library was screened with a radioactively labelled probe representing around 200 bp of the catalase sequence. Approximately 8000 plaques were screened resulting in the detection of eight positive clones. These were picked, purified and the expression plasmid pBK-CMV excised for further characterisation. The proteins expressed by the recombinant plasmids were analysed by Western blotting. Of the eight clones tested, five possessed an extremely immunoreactive band at approximately 50,000 Da (the size expected for catalase).

To investigate whether this immunoreactivity correlated with biological activity, bacterial colonies representing a positive and a negative reaction were tested for catalase activity by the addition of hydrogen peroxide. The immunoreactive clone exhibited an explosive bubbling action whilst the non-immunoreactive clone remained unchanged. From this data it was assumed that the positive clone contained the complete coding sequence for catalase and this clone was further characterised by restriction mapping and DNA sequencing. To enable localisation of the catalase coding sequence, the DNA sequence of the 200 bp probe fragment was obtained and useful restrictions sites were identified for mapping (HindIII, BstXI, PflMI). From this data both the direction and approximate position of the gene could be deduced. DNA sequence analysis confirmed the mapping data and the catalase sequence coding for a protein of predicted molecular weight of 58,650 Da is shown in SEQ ID NO. 1 and 2.

2. Identification of *E. coli* Clones Expressing Catalase From *H. pylori* Isolate RU1.

2.1 Materials and Methods

To obtain the catalase gene from *H. pylori* isolate RU1, genomic DNA from *H. pylori* isolate RU1 was partially digested with Sau3A and cloned into the A-ZAP Express vector (Stratagene). This genomic library was probed with a 711 bp fragment of the *H. pylori* catalase ORF, which was generated by PCR using primers starting at nucleotide 1 (21 mer) and terminating at nucleotide 711 (18 mer), and labelled with dioxigenin-dUTP (Boehringer Mannheim).

Catalase positive cones were excised into phagemid form and introduced into the XLOLR *E. coli* strain (Stratagene). Clones which produced a functional catalase were selected by placing the cells into 30% $H_2O_2$ and checking for the rapid formation of oxygen. The selected strain was maintained on Luria agar containing 50 mg/L Kanamycin sulfate (Gibco BRL).

For recombinant catalase purification, the recombinant *E. coli* strain was grown in Luria broth plus Kanamycin, and purified using the method of Hazell et al[10].

DNA sequence analysis was performed by manual sequencing on both strands of plasmid DNA by primer walk using the deoxynucleotide chain termination method[14].

2.2 Results

DNA sequence analysis identified a sequence coding for a protein of predicted molecular weight of 58,650 Da, which is shown in SEQ ID NO. 3 and 4.

3. Protective Efficacy of Recombinant *H. Pylori* Catalase From Isolate RU1

3.1 Materials and Methods 3.1.1 Immunisation with Recombinant *H. pylori* Catalase Sufficient purified catalase (from isolate RU1) for immunising 10 mice was pooled. Female SPS BALB/c mice were given 0.2 mg purified catalase+10 µg cholera toxin (CT) 4 times on days 0, 7, 14 and 21. Control groups were: *H. pylori* whole cell sonicate+CT (positive control), *E. coli* and PBS buffer alone (negative controls). The dose size was 150 µl for mice dosed with catalase and 100 µl for those animals receiving other preparations. On the day of each immunising dose, the catalase was checked for activity using $H_2O_2$ and for any signs of degradation using SDS-PAGE and Coomassie Blue staining. No signs of declining activity or any degradation was observed throughout the immunisation course. Three weeks after the last immunising dose the groups were challenged with two doses of $\sim 10^8$ *H. pylori* (Sydney strain), given 48 hours apart. Three weeks later mice were euthanased and samples (sera, saliva, bile and the stomach—half for histology and half the antrum for the direct urease tests[3]) were collected. The histology samples were fixed in 10% buffered formalin, paraffin embedded and stained using the May-Grüwald Giemsa stain. Stomach sections were scanned for *H. pylori* using light microscopy (1000 x magnification) and scored as infected if one or more organisms were detected in either the gastric body or antrum.

3.1.2 Experimental Outline

| Day | rCat + CT [n = 10] | Hp + CT [n = 10] | *E. coli* + CT [n = 10] | PBS Alone [n = 10] | Norm [n = 10] |
|---|---|---|---|---|---|
| 0 | rCat + CT | Hp + CT | *E. coli* + CT | PBS Alone | — |
| 7 | rCat + CT | Hp + CT | *E. coli* + CT | PBS Alone | — |
| 14 | rCat + CT | Hp + CT | *E. coli* + CT | PBS Alone | — |
| 21 | rCat + CT | Hp + CT | *E. coli* + CT | PBS Alone | — |
| 42 | | *H. pylori* Challenge | | | — |
| 44 | | *H. pylori* Challenge | | | — |
| 58 | | Collect all groups | | | Collect |

3.2 Results and Discussion

Infection was assessed by testing samples of antral mucosa in the rapid microtitre urease test as described in Lee et al.[3] and by direct microscopic examination. The urease test has been validated as being highly predictive of Helicobacter infection Urease positivity indicates Helicobacter infection. Mice were scored as infected if positive in either test.

| GROUP | No. Infected (%) |
| --- | --- |
| Catalase + CT | 1/10 (10) |
| XLOLR + CT | 9/10 (90) |
| PBS Alone | 10/10 (80) |
| H. pylori + CT | 2/10 (10) |
| Normal (unchallenged) | 0/8 (0) |

This experiment indicates that recombinant H. pylori catalase is an effective protective antigen for immunisation against H. pylori infection.

Previous results with sonicates of whole helicobacter cells[4] and the results of Corthesy-Theulaz et al.[15] with a recombinant helicobacter antigen, urease, show that antigens that have a protective, or prophylactic effect to prevent new infections, also can be used therapeutically to treat current infections. Therefore it is expected that catalase could be used both as a protective antigen in a vaccine to prevent infection, and in an immunotherapeutic composition or therapeutic vaccine to treat infected persons.

References

1. Helicobacter pylori Biology and Clinical Practice (1993). Edited by C. Stewart Goodwin and Bryan W. Worsley. Published by CRC Press.
2. Halter, F., Hurlimann, S. and Inauen, W. (1992). Pathophysiology and clinical relevance of Helicobacter pylori. The Yale Journal of Biology and Medicine, 65:625–638.
3. Lee, A., Fox, J. G., Otto, G. and Murphy, J. (1990). A small animal model of human Helicobacter pylori active chronic gastritis. Gastroenterology, 99:1316–1323.
4. Doidge, C. G., Gust, I., Lee, A., Buck, F., Hazel, S. and Mane, U. (1994). Therapeutic immunisation against Helicobacter pylori—The first evidence. Lancet 343(i): 914–915.
5. Clayton, C. L., Pallen, M. J., Kleanthous, H., Wren, B. W. and Tabaqchali, S. (1990). Nucleotide sequence of two genes from Helicobacter pylori encoding for urease subunits. Nucleic Acid Res., 18(2):362
6. Westblom, T. U., Phadnis, S., Langenberg, W., Yondea, K., Madan, E. and Midkiff, B. R. (1992). Catalase negative mutants of Helicobacter pylori. European Journal of Clinical Microbiology and Infectious Diseases, 11:522–526.
7. Cox, J. and Coulter, A. (1992). Advances in adjuvant technology and application. In Animal Parasite Control Using Biotechnology. Edited by W. K. Yong. Published by CRC Press.
8. Holmgren, J., Czerkinsky, C., Lycke, N. and Svennerholm, A. M. (1992). Mucosal Immunity: Implications for Vaccine Development, Immunobiol. 184 157–179.
9. McGhee, J. R., Mestecky, J., Dertzbaugh, M. T., Eldridge, J. H., Hirasawa, M. and Kiyono, H. (1992). The mucosal immune system: from fundamental concepts to vaccine development. Vaccine 10(2):75–88.
10. Hazell, S. L., Evans Jr., D. J. and Graham, D. Y. (1991). Helicobacter pylori catalase. J. Gen. Microbiol. 137:57–61.
11. Majewski, S. L. H., and Goodwin, C. S. (1988). Restriction endonuclease analysis of the genome of Campylobacter pylori with a rapid extraction method: evidence for considerable genomic variation. J. Inf. Dis. 157(3):465–471.
12. Sambrook, J., Fritsch, E. F. and Maniatis, T. (1989). Molecular Cloning: A Laboratory Manual, 2nd edn. Cold Spring Harbor, N.Y.: Cold Spring Harbor Laboratory Press.
13. Towbin, H., Staehelin, T. and Gordon, J. (1979). Electrophoretic transfer of proteins from polyacrylamide gels to nitrocellulose sheets: procedure and some applications. Proc.Natl.Acad. Sci. USA 74:4350–4354.
14. Sanger, F., Nicklen, S. and Coulson, A. R. (1977). DNA sequencing with chain-terminating inhibitors. Proc.Natl. Acad. Sci. USA 74:5463–5467.
15. Corthésy-Theulaz, I, Porta, N., Glauser, M. Saraga, E., Vaney, A. C., Haas, R., Kraehenbuhl, J. P., Blum, A. L. and Michetti, P., (1995). Oral Immunisation With Helicobacter pylori Urease B Subunit as a Treatment Against Helicobacter Infection in Mice. Gastroenterology 109:115–121.

What is claimed is:

1. A composition for use in the treatment or prevention of Helicobacter infection in a mammalian host, which comprises an immunologically effective amount of a preparation of substantially pure, full-length Helicobacter catalase, wherein the catalase content is at least 80% of the total Helicobacter antigens in the preparation, together with a muscosal adjuvant and a pharmaceutically acceptable carrier or diluent.

2. A composition according to claim 1, wherein the catalase is *Helicobacter pylori* catalase.

3. A composition according to claim 1, wherein the catalase is recombinant catalase.

4. A composition according to claim 1, which further comprises at least one additional immunogen.

5. A composition according to claim 4, wherein said additional immunogen is a Helicobacter antigen.

6. A composition according to claim 5, wherein said additional immunogen is selected from Helicobacter urease and Helicobacter lipopolysaccharide.

7. A method for the treatment or prevention of Helicobacter infection in a mammalian host, which comprises mucosal administration to said host of an immunologically effective amount of a composition which comprises a preparation of substantially pure, full-length Helicobacter catalase, wherein the catalase content is at least 80% of the total Helicobacter antigens in the preparation, together with a mucosal adjuvant and a pharmaceutically acceptable carrier or diluent.

8. A method according to claim 7, wherein the catalase is *Helicobacter pylori* catalase.

9. A method according to claim 7, wherein the catalase is recombinant catalase.

10. A method according to claim 7, wherein said composition further comprises at least one additional immunogen.

11. A method according to claim 10, wherein said additional immunogen is another Helicobacter antigen.

12. A method according to claim 11, wherein said additional immunogen is selected from Helicobacter urease and Helicobacter lipopolysaccharide.

13. A method according to claim 7, wherein said composition is orally administered to said host.

14. A method according to claim 7, wherein said host is a human.

15. A method of producing a vaccine composition comprising the step of bringing a composition comprising a preparation of substantially pure, full-length Helicobacter catalase, wherein the catalase content is at least 80% of the total Helicobacter antigens in the preparation, together with a mucosal adjuvant and a pharmaceutically acceptable carrier or diluent, into a form suitable for administration to a mammalian host.

16. A method according to claim 15, wherein the catalase is *Helicobacter pylori catalase*.

17. A method according to claim 15, wherein the catalase is recombinant catalase.

18. A method according to claim 15, wherein the composition further comprises at least one additional immunogen.

19. A method according to claim 18, wherein said additional immunogen is another Helicobacter antigen.

20. A method according to claim 19, wherein said additional immunogen is selected from Helicobacter urease and Helicobacter lipopolysaccharide.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 1518 base pairs
      (B) TYPE: nucleic acid
      (C) STRANDEDNESS: single
      (D) TOPOLOGY: linear (vi) ORIGINAL SOURCE:
      (A) ORGANISM: Heliobacter pylori
      (B) STRAIN: HP 921023

(ix) FEATURE:
      (A) NAME/KEY: CDS
      (B) LOCATION: 1..1515

(ix) FEATURE:
      (A) NAME/KEY: mat_peptide (B) LOCATION: 1..1515

(xi) SEQUENCE DESCRIPTION: SEQ ID NO: 1:

```
ATG GTT AAT AAA GAT GTG AAA CAA ACC ACT GCT TTT GGC ACT CCC GTT        48
Met Val Asn Lys Asp Val Lys Gln Thr Thr Ala Phe Gly Thr Pro Val
 1               5                  10                  15

TGG GAT GAC AAC AAT GTG ATT ACG GCC GGC CCT AGA GGT CCT GTT TTA        96
Trp Asp Asp Asn Asn Val Ile Thr Ala Gly Pro Arg Gly Pro Val Leu
                20                  25                  30

TTA CAA AGC ACT TGG TTT TTG GAA AAG TTA GCG GCG TTT GAC AGA GAA       144
Leu Gln Ser Thr Trp Phe Leu Glu Lys Leu Ala Ala Phe Asp Arg Glu
            35                  40                  45

AGG ATC CCT GAA AGG GTG GTG CAT GCT AAA GGA AGC GGG GCT TAT GGC       192
Arg Ile Pro Glu Arg Val Val His Ala Lys Gly Ser Gly Ala Tyr Gly
        50                  55                  60

ACT TTC ACC GTG ACT AAA GAC ATC ACT AAA TAC ACT AAA GCG AAA ATT       240
Thr Phe Thr Val Thr Lys Asp Ile Thr Lys Tyr Thr Lys Ala Lys Ile
 65                  70                  75                  80

TTC TCT AAA GTG GGC AAA AAA ACA GAA TGC TTC TTC AGA TTT TCT ACT       288
Phe Ser Lys Val Gly Lys Lys Thr Glu Cys Phe Phe Arg Phe Ser Thr
                85                  90                  95

GTG GCT GGT GAA AGA GGC AGT GCG GAT GCG GTA AGA GAC CCT AGA GGT       336
Val Ala Gly Glu Arg Gly Ser Ala Asp Ala Val Arg Asp Pro Arg Gly
            100                 105                 110

TTT GCG ATG AAG TAT TAC ACT GAA GAA GGT AAC TGG GAT TTA GTG GGG       384
Phe Ala Met Lys Tyr Tyr Thr Glu Glu Gly Asn Trp Asp Leu Val Gly
        115                 120                 125

AAC AAC ACG CCT GTT TTC TTT ATC CGT GAT GCG ATC AAA TTC CCT GAT       432
Asn Asn Thr Pro Val Phe Phe Ile Arg Asp Ala Ile Lys Phe Pro Asp
130                 135                 140

TTC ATC CAC ACT CAA AAA CGA GAT CCT CAA ACC AAT TTG CCT AAC CAT       480
Phe Ile His Thr Gln Lys Arg Asp Pro Gln Thr Asn Leu Pro Asn His
145                 150                 155                 160

GAC ATG GTA TGG GAT TTT TGG AGC AAT GTT CCT GAA AGC TTA TAC CAA       528
Asp Met Val Trp Asp Phe Trp Ser Asn Val Pro Glu Ser Leu Tyr Gln
                165                 170                 175

GTA ACA TGG GTT ATG AGC GAT AGA GGT ATC CCT AAA TCT TTC CGC CAC       576
Val Thr Trp Val Met Ser Asp Arg Gly Ile Pro Lys Ser Phe Arg His
            180                 185                 190

ATG GAT GGT TTT GGC AGC CAC ACT TTC AGT CTT ATC AAC GCT AAA GGC       624
Met Asp Gly Phe Gly Ser His Thr Phe Ser Leu Ile Asn Ala Lys Gly
        195                 200                 205

GAA CGC TTT TGG GTG AAA TTC CAC TTT GAA ACC ATG CAA GGC GTT AAG       672
Glu Arg Phe Trp Val Lys Phe His Phe Glu Thr Met Gln Gly Val Lys
        210                 215                 220

CAC TTG ACT AAC GAA GAA GCC GCA GAA ATC AGA AAG CAT GAT CCC GAT       720
His Leu Thr Asn Glu Glu Ala Ala Glu Ile Arg Lys His Asp Pro Asp
225                 230                 235                 240

TCC AAT CAA AGG GAT TTA TTC AAT GCG ATC GCT AGA GGG GAT TTC CCA       768
Ser Asn Gln Arg Asp Leu Phe Asn Ala Ile Ala Arg Gly Asp Phe Pro
                245                 250                 255

AAA TGG AAA TTA AGC ATT CAA GTG ATG CCA GAA GAG GAC GCT AAG AAG       816
Lys Trp Lys Leu Ser Ile Gln Val Met Pro Glu Glu Asp Ala Lys Lys
            260                 265                 270

TAT CGA TTC CAT CCG TTT GAT GTT ACT AAA ATT TGG TAT CTC CAA GAT       864
Tyr Arg Phe His Pro Phe Asp Val Thr Lys Ile Trp Tyr Leu Gln Asp
        275                 280                 285

TAT CCA TTG ATG GAA GTG GGC ATT GTA GAG TTG AAT AAA AAT CCC GAA       912
Tyr Pro Leu Met Glu Val Gly Ile Val Glu Leu Asn Lys Asn Pro Glu
        290                 295                 300
```

```
AAC TAT TTC GCA GAA GTG GAG CAA GCG GCA TTC AGT CCG GCT AAT GTC      960
Asn Tyr Phe Ala Glu Val Glu Gln Ala Ala Phe Ser Pro Ala Asn Val
305             310                 315                 320

GTT CCT GGA ATT GGC TAT AGC CCT GAT AGG ATG TTA CAA GGG CGC TTG     1008
Val Pro Gly Ile Gly Tyr Ser Pro Asp Arg Met Leu Gln Gly Arg Leu
            325                 330                 335

TTC TCT TAT GGA GAC ACA CAC CGC TAC CGC TTA GGG GTT AAT TAT CCT     1056
Phe Ser Tyr Gly Asp Thr His Arg Tyr Arg Leu Gly Val Asn Tyr Pro
                340                 345                 350

CAA ATA CCG GTT AAT AAA CCA AGA TGC CCG TTC CAC TCT TCT AGC AGA     1104
Gln Ile Pro Val Asn Lys Pro Arg Cys Pro Phe His Ser Ser Ser Arg
            355                 360                 365

GAT GGT TAC ATG CAA AAC GGG TAT TAC GGC TCT TTA CAA AAC TAT ACG     1152
Asp Gly Tyr Met Gln Asn Gly Tyr Tyr Gly Ser Leu Gln Asn Tyr Thr
370             375                 380

CCT AGC TCA TTG CCT GGC TAT AAA GAA GAT AAG AGT GCA AGG GAT CCT     1200
Pro Ser Ser Leu Pro Gly Tyr Lys Glu Asp Lys Ser Ala Arg Asp Pro
385             390                 395                 400

AAG TTC AAC TTA GCT CAT ATT GAG AAA GAG TTT GAA GTG TGG AAT TGG     1248
Lys Phe Asn Leu Ala His Ile Glu Lys Glu Phe Glu Val Trp Asn Trp
                405                 410                 415

GAT TAC AGA GCT GAG GAT AGC GAT TAC TAC ACC CAA CCA GGT GAT TAC     1296
Asp Tyr Arg Ala Glu Asp Ser Asp Tyr Tyr Thr Gln Pro Gly Asp Tyr
            420                 425                 430

TAC CGC TCA TTG CCA GCT GAT GAA AAA GAA AGG TTG CAT GAC ACT ATT     1344
Tyr Arg Ser Leu Pro Ala Asp Glu Lys Glu Arg Leu His Asp Thr Ile
            435                 440                 445

GGA GAG TCT TTA GCT CAT GTT ACC CAT AAG GAA ATT GTG GAT AAA CAA     1392
Gly Glu Ser Leu Ala His Val Thr His Lys Glu Ile Val Asp Lys Gln
450             455                 460

TTG GAG CAT TTC AAG AAA GCT GAC CCC AAA TAC GCT GAG GGA GTT AAA     1440
Leu Glu His Phe Lys Lys Ala Asp Pro Lys Tyr Ala Glu Gly Val Lys
465             470                 475                 480

AAA GCT CTT GAA AAA CAC CAA AAA ATG ATG AAA GAC ATG CAT GGA AAA     1488
Lys Ala Leu Glu Lys His Gln Lys Met Met Lys Asp Met His Gly Lys
                485                 490                 495

GAC ATG CAC CAC ACG AAA AAG AAA AAG TAA                             1518
Asp Met His His Thr Lys Lys Lys Lys
                500                 505

(2) INFORMATION FOR SEQ ID NO: 2:

(i) SEQUENCE CHARACTERISTICS:
        (A) LENGTH: 505 amino acids
        (B) TYPE: amino acid
        (D) TOPOLOGY: linear (ii) MOLECULE TYPE: protein (xi) SEQUENCE DESCRIPTION: SEQ ID NO: 2:

Met Val Asn Lys Asp Val Lys Gln Thr Thr Ala Phe Gly Thr Pro Val
1               5                   10                  15

Trp Asp Asp Asn Asn Val Ile Thr Ala Gly Pro Arg Gly Pro Val Leu
                20                  25                  30

Leu Gln Ser Thr Trp Phe Leu Glu Lys Leu Ala Ala Phe Asp Arg Glu
            35                  40                  45

Arg Ile Pro Glu Arg Val His Ala Lys Gly Ser Gly Ala Tyr Gly
        50                  55                  60

Thr Phe Thr Val Thr Lys Asp Ile Thr Lys Tyr Thr Lys Ala Lys Ile
65              70                  75                  80
```

```
Phe Ser Lys Val Gly Lys Lys Thr Glu Cys Phe Phe Arg Phe Ser Thr
                    85                  90                  95
Val Ala Gly Glu Arg Gly Ser Ala Asp Ala Val Arg Asp Pro Arg Gly
                100                 105                 110
Phe Ala Met Lys Tyr Tyr Thr Glu Glu Gly Asn Trp Asp Leu Val Gly
                115                 120                 125
Asn Asn Thr Pro Val Phe Phe Ile Arg Asp Ala Ile Lys Phe Pro Asp
        130                 135                 140
Phe Ile His Thr Gln Lys Arg Asp Pro Gln Thr Asn Leu Pro Asn His
145                 150                 155                 160
Asp Met Val Trp Asp Phe Trp Ser Asn Val Pro Glu Ser Leu Tyr Gln
                165                 170                 175
Val Thr Trp Val Met Ser Asp Arg Gly Ile Pro Lys Ser Phe Arg His
                180                 185                 190
Met Asp Gly Phe Gly Ser His Thr Phe Ser Leu Ile Asn Ala Lys Gly
                195                 200                 205
Glu Arg Phe Trp Val Lys Phe His Phe Glu Thr Met Gln Gly Val Lys
            210                 215                 220
His Leu Thr Asn Glu Glu Ala Glu Ile Arg Lys His Asp Pro Asp
225                 230                 235                 240
Ser Asn Gln Arg Asp Leu Phe Asn Ala Ile Ala Arg Gly Asp Phe Pro
                245                 250                 255
Lys Trp Lys Leu Ser Ile Gln Val Met Pro Glu Glu Asp Ala Lys Lys
                260                 265                 270
Tyr Arg Phe His Pro Phe Asp Val Thr Lys Ile Trp Tyr Leu Gln Asp
                275                 280                 285
Tyr Pro Leu Met Glu Val Gly Ile Val Glu Leu Asn Lys Asn Pro Glu
        290                 295                 300
Asn Tyr Phe Ala Glu Val Glu Gln Ala Ala Phe Ser Pro Ala Asn Val
305                 310                 315                 320
Val Pro Gly Ile Gly Tyr Ser Pro Asp Arg Met Leu Gln Gly Arg Leu
                325                 330                 335
Phe Ser Tyr Gly Asp Thr His Arg Tyr Arg Leu Gly Val Asn Tyr Pro
                340                 345                 350
Gln Ile Pro Val Asn Lys Pro Arg Cys Pro Phe His Ser Ser Ser Arg
        355                 360                 365
Asp Gly Tyr Met Gln Asn Gly Tyr Tyr Gly Ser Leu Gln Asn Tyr Thr
        370                 375                 380
Pro Ser Ser Leu Pro Gly Tyr Lys Glu Asp Lys Ser Ala Arg Asp Pro
385                 390                 395                 400
Lys Phe Asn Leu Ala His Ile Glu Lys Glu Phe Glu Val Trp Asn Trp
                405                 410                 415
Asp Tyr Arg Ala Glu Asp Ser Asp Tyr Tyr Thr Gln Pro Gly Asp Tyr
                420                 425                 430
Tyr Arg Ser Leu Pro Ala Asp Gly Lys Glu Arg Leu His Asp Thr Ile
                435                 440                 445
Gly Glu Ser Leu Ala His Val Thr His Lys Glu Ile Val Asp Lys Gln
        450                 455                 460
Leu Glu His Phe Lys Lys Ala Asp Pro Lys Tyr Ala Glu Gly Val Lys
465                 470                 475                 480
Lys Ala Leu Glu Lys His Gln Lys Met Met Lys Asp Met His Gly Lys
                485                 490                 495
```

```
Asp Met His His Thr Lys Lys Lys Lys
        500                 505
```

(2) INFORMATION FOR SEQ ID NO: 3:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (vi) ORIGINAL SOURCE:
        (A) ORGANISM: Heliobacter pylori
        (B) STRAIN: RU1

(ix) FEATURE:
        (A) NAME/KEY: CDS
        (B) LOCATION: 1..1515

(ix) FEATURE:
        (A) NAME/KEY: mat_peptide
        (B) LOCATION: 1..1515

(xi) SEQUENCE DESCRIPTION: SEQ ID NO: 3:

```
ATG GTT AAT AAA GAT GTG AAA CAA ACC ACT GCT TTT GGC GCT CCC GTT        48
Met Val Asn Lys Asp Val Lys Gln Thr Thr Ala Phe Gly Ala Pro Val
 1               5                  10                  15

TGG GAT GAT AAC AAT GTG ATT ACG GCT GGT CCT AGA GGT CCT GTT TTA        96
Trp Asp Asp Asn Asn Val Ile Thr Ala Gly Pro Arg Gly Pro Val Leu
                20                  25                  30

TTA CAA AGC ACT TGG TTT TTG GAA AAG TTA GCA GCG TTT GAC AGA GAA       144
Leu Gln Ser Thr Trp Phe Leu Glu Lys Leu Ala Ala Phe Asp Arg Glu
            35                  40                  45

AGG ATC CCT GAA AGG GTA GTG CAT GCT AAA GGA AGC GGG GCT TAT GGC       192
Arg Ile Pro Glu Arg Val Val His Ala Lys Gly Ser Gly Ala Tyr Gly
        50                  55                  60

ACT TTC ACC GTG ACT AAA GAC ATC ACT AAA TAC ACT AAA GCG AAG ATT       240
Thr Phe Thr Val Thr Lys Asp Ile Thr Lys Tyr Thr Lys Ala Lys Ile
 65                  70                  75                  80

TTC TCT AAA GTG GGC AAA AAA ACC GAA TGC TTT TTC AGG TTT TCT ACT       288
Phe Ser Lys Val Gly Lys Lys Thr Glu Cys Phe Phe Arg Phe Ser Thr
                85                  90                  95

GTG GCT GGT GAA AGA GGC AGT GCG GAT GCA GTG AGA GAC CCT AGA GGT       336
Val Ala Gly Glu Arg Gly Ser Ala Asp Ala Val Arg Asp Pro Arg Gly
            100                 105                 110

TTT GCG ATG AAG TAT TAC ACT GAA GAA GGT AAC TGG GAT TTA GTA GGG       384
Phe Ala Met Lys Tyr Tyr Thr Glu Glu Gly Asn Trp Asp Leu Val Gly
        115                 120                 125

AAC AAC ACG CCT GTT TTC TTT ATC CGT GAT GCG ATC AAA TTC CCT GAT       432
Asn Asn Thr Pro Val Phe Phe Ile Arg Asp Ala Ile Lys Phe Pro Asp
130                 135                 140

TTC ATC CAC ACC CAA AAA AGA GAC CCT CAA ACC AAT TTG CCT AAC CAC       480
Phe Ile His Thr Gln Lys Arg Asp Pro Gln Thr Asn Leu Pro Asn His
145                 150                 155                 160

GAC ATG GTA TGG GAT TTT TGG AGT AAT GTT CCT GAA AGC TTG TAT CAA       528
Asp Met Val Trp Asp Phe Trp Ser Asn Val Pro Glu Ser Leu Tyr Gln
                165                 170                 175

GTA ACA TGG GTT ATG AGC GAT AGA GGG ATC CCT AAA TCT TTC CGC CAC       576
Val Thr Trp Val Met Ser Asp Arg Gly Ile Pro Lys Ser Phe Arg His
            180                 185                 190

ATG GAT GGT TTT GGC AGC CAC ACT TTC AGT CTT ATC AAC GCT AAG GGC       624
Met Asp Gly Phe Gly Ser His Thr Phe Ser Leu Ile Asn Ala Lys Gly
        195                 200                 205

GAA CGC TTT TGG GTG AAA TTC CAC TTT CAC ACC ATG CAA GGC GTT AAG       672
```

```
Glu Arg Phe Trp Val Lys Phe His Phe His Thr Met Gln Gly Val Lys
    210                 215                 220

CAC TTG ACT AAC GAA GAA GCC GCA GAA GTC AGA AAA TAT GAT CCT GAT        720
His Leu Thr Asn Glu Glu Ala Ala Glu Val Arg Lys Tyr Asp Pro Asp
225                 230                 235                 240

TCC AAT CAA AGG GAT TTA TTC AAT GCG ATC GCT AGA GGG GAT TTC CCA        768
Ser Asn Gln Arg Asp Leu Phe Asn Ala Ile Ala Arg Gly Asp Phe Pro
                245                 250                 255

AAA TGG AAA TTA AGC ATT CAA GTG ATG CCA GAA GAA GAT GCT AAG AAG        816
Lys Trp Lys Leu Ser Ile Gln Val Met Pro Glu Glu Asp Ala Lys Lys
                    260                 265                 270

TAT CGA TTC CAT CCG TTT GAT GTT ACT AAA ATT TGG TAT CTC CAA GAT        864
Tyr Arg Phe His Pro Phe Asp Val Thr Lys Ile Trp Tyr Leu Gln Asp
            275                 280                 285

TAT CCG TTG ATG GAA GTG GGC ATT GTA GAG TTG AAT AAA AAT CCA GAA        912
Tyr Pro Leu Met Glu Val Gly Ile Val Glu Leu Asn Lys Asn Pro Glu
        290                 295                 300

AAC TAT TTT GCA GAA GTG GAG CAA GTG GCA TTC ACT CCG GCT AAT GTC        960
Asn Tyr Phe Ala Glu Val Glu Gln Val Ala Phe Thr Pro Ala Asn Val
305                 310                 315                 320

GTT CCT GGA ATT GGC TAT AGC CCT GAT AGG ATG TTA CAA GGA CGC TTG       1008
Val Pro Gly Ile Gly Tyr Ser Pro Asp Arg Met Leu Gln Gly Arg Leu
                325                 330                 335

TTC TCT TAT GGG GAC ACA CAC CGC TAC CGC TTA GGG GTT AAT TAT CCT       1056
Phe Ser Tyr Gly Asp Thr His Arg Tyr Arg Leu Gly Val Asn Tyr Pro
                    340                 345                 350

CAA ATA CCG GTT AAT AAA CCA AGA TGC CCG TTC CAC TCT TCT AGC AGA       1104
Gln Ile Pro Val Asn Lys Pro Arg Cys Pro Phe His Ser Ser Ser Arg
            355                 360                 365

GAT GGT TAC ATG CAA AAC GGA TAC TAC GGC TCT TTA CAA AAC TAT ACG       1152
Asp Gly Tyr Met Gln Asn Gly Tyr Tyr Gly Ser Leu Gln Asn Tyr Thr
        370                 375                 380

CCT AGC TCA TTG CCA GGT TAT AAA GAA GAT AAG AGC GCG AGA GAT CCT       1200
Pro Ser Ser Leu Pro Gly Tyr Lys Glu Asp Lys Ser Ala Arg Asp Pro
385                 390                 395                 400

AAG TTC AAC TTA GCT CAT ATT GAG AAA GAG TTT GAA GTG TGG AAT TGG       1248
Lys Phe Asn Leu Ala His Ile Glu Lys Glu Phe Glu Val Trp Asn Trp
                405                 410                 415

GAT TAC AGG GCT GAT GAT AGC GAT TAC TAC ACC CAA CCA GGT GAT TAC       1296
Asp Tyr Arg Ala Asp Asp Ser Asp Tyr Tyr Thr Gln Pro Gly Asp Tyr
                    420                 425                 430

TAC CGC TCA TTG CCA GCT GAT GAA AAA GAA AGG TTG CAT GAC ACT ATT       1344
Tyr Arg Ser Leu Pro Ala Asp Glu Lys Glu Arg Leu His Asp Thr Ile
            435                 440                 445

GGA GAG TCT TTG GCT CAT GTT ACC CAT AAG GAA ATT GTG GAT AAA CAA       1392
Gly Glu Ser Leu Ala His Val Thr His Lys Glu Ile Val Asp Lys Gln
        450                 455                 460

TTG GAG CAT TTC AAG AAA GCT GAT CCC AAA TAC GCT GAG GGA GTT AAA       1440
Leu Glu His Phe Lys Lys Ala Asp Pro Lys Tyr Ala Glu Gly Val Lys
465                 470                 475                 480

AAA GCT CTT GAA AAA CAC CAA AAG ATG ATG AAA GAC ATG CAT GGA AAA       1488
Lys Ala Leu Glu Lys His Gln Lys Met Met Lys Asp Met His Gly Lys
                485                 490                 495

GAC ATG CAC CAC ACA AAA AAG AAA AAG TAA                                1518
Asp Met His His Thr Lys Lys Lys Lys
                500                 505

(2) INFORMATION FOR SEQ ID NO: 4:

(i) SEQUENCE CHARACTERISTICS:
```

(A) LENGTH: 505 amino acids
       (B) TYPE: amino acid
       (D) TOPOLOGY: linear (ii) MOLECULE TYPE: protein (xi) SEQUENCE DESCRIPTION: SEQ ID NO: 4:

Met Val Asn Lys Asp Val Lys Gln Thr Thr Ala Phe Gly Ala Pro Val
 1               5                  10                  15

Trp Asp Asp Asn Asn Val Ile Thr Ala Gly Pro Arg Gly Pro Val Leu
                20                  25                  30

Leu Gln Ser Thr Trp Phe Leu Glu Lys Leu Ala Ala Phe Asp Arg Glu
            35                  40                  45

Arg Ile Pro Glu Arg Val Val His Ala Lys Gly Ser Gly Ala Tyr Gly
 50                  55                  60

Thr Phe Thr Val Thr Lys Asp Ile Thr Lys Tyr Thr Lys Ala Lys Ile
 65                  70                  75                  80

Phe Ser Lys Val Gly Lys Lys Thr Glu Cys Phe Phe Arg Phe Ser Thr
                85                  90                  95

Val Ala Gly Glu Arg Gly Ser Ala Asp Ala Val Arg Asp Pro Arg Gly
            100                 105                 110

Phe Ala Met Lys Tyr Tyr Thr Glu Glu Gly Asn Trp Asp Leu Val Gly
        115                 120                 125

Asn Asn Thr Pro Val Phe Phe Ile Arg Asp Ala Ile Lys Phe Pro Asp
130                 135                 140

Phe Ile His Thr Gln Lys Arg Asp Pro Gln Thr Asn Leu Pro Asn His
145                 150                 155                 160

Asp Met Val Trp Asp Phe Trp Ser Asn Val Pro Glu Ser Leu Tyr Gln
                165                 170                 175

Val Thr Trp Val Met Ser Asp Arg Gly Ile Pro Lys Ser Phe Arg His
            180                 185                 190

Met Asp Gly Phe Gly Ser His Thr Phe Ser Leu Ile Asn Ala Lys Gly
        195                 200                 205

Glu Arg Phe Trp Val Lys Phe His Phe His Thr Met Gln Gly Val Lys
210                 215                 220

His Leu Thr Asn Glu Glu Ala Ala Glu Val Arg Lys Tyr Asp Pro Asp
225                 230                 235                 240

Ser Asn Gln Arg Asp Leu Phe Asn Ala Ile Ala Arg Gly Asp Phe Pro
                245                 250                 255

Lys Trp Lys Leu Ser Ile Gln Val Met Pro Glu Glu Asp Ala Lys Lys
            260                 265                 270

Tyr Arg Phe His Pro Phe Asp Val Thr Lys Ile Trp Tyr Leu Gln Asp
        275                 280                 285

Tyr Pro Leu Met Glu Val Gly Ile Val Glu Leu Asn Lys Asn Pro Glu
290                 295                 300

Asn Tyr Phe Ala Glu Val Glu Gln Val Ala Phe Thr Pro Ala Asn Val
305                 310                 315                 320

Val Pro Gly Ile Gly Tyr Ser Pro Asp Arg Met Leu Gln Gly Arg Leu
                325                 330                 335

Phe Ser Tyr Gly Asp Thr His Arg Tyr Arg Leu Gly Val Asn Tyr Pro
            340                 345                 350

Gln Ile Pro Val Asn Lys Pro Arg Cys Pro Phe His Ser Ser Ser Arg
        355                 360                 365

Asp Gly Tyr Met Gln Asn Gly Tyr Tyr Gly Ser Leu Gln Asn Tyr Thr
370                 375                 380

```
Pro Ser Ser Leu Pro Gly Tyr Lys Glu Asp Lys Ser Ala Arg Asp Pro
385                 390                 395                 400

Lys Phe Asn Leu Ala His Ile Glu Lys Glu Phe Glu Val Trp Asn Trp
                405                 410                 415

Asp Tyr Arg Ala Asp Asp Ser Asp Tyr Tyr Thr Gln Pro Gly Asp Tyr
            420                 425                 430

Tyr Arg Ser Leu Pro Ala Asp Glu Lys Glu Arg Leu His Asp Thr Ile
        435                 440                 445

Gly Glu Ser Leu Ala His Val Thr His Lys Glu Ile Val Asp Lys Gln
    450                 455                 460

Leu Glu His Phe Lys Lys Ala Asp Pro Lys Tyr Ala Glu Gly Val Lys
465                 470                 475                 480

Lys Ala Leu Glu Lys His Gln Lys Met Met Lys Asp Met His Gly Lys
                485                 490                 495

Asp Met His His Thr Lys Lys Lys Lys
                500                 505

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 5:

Met Lys Lys Ile Val Phe Lys Glu Tyr Val
1               5                   10

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO: 6:

Met Val Asn Lys Asp Val Lys Gln Thr Thr Ala Phe Gly Thr Pro
1               5                   10                  15
```